United States Patent [19]

Rogers et al.

[11] 4,435,583
[45] Mar. 6, 1984

[54] 2-HALO-SUBSTITUTED MONIC ACID A USEFUL AS ANTIBACTERIAL COMPOUNDS

[75] Inventors: Norman H. Rogers; Michael J. Crimmin, both of Horsham, England

[73] Assignee: Beecham Group p.l.c., England

[21] Appl. No.: 447,516

[22] Filed: Dec. 7, 1982

[30] Foreign Application Priority Data

Dec. 9, 1981 [GB] United Kingdom ............... 8137147

[51] Int. Cl.$^3$ .................... C07D 309/06; A61K 31/35
[52] U.S. Cl. ...................................... 549/414; 424/283
[58] Field of Search ......................................... 549/414

[56] References Cited

U.S. PATENT DOCUMENTS 4,312,867  1/1982  Rogers et al. .................. 549/414
4,374,147  2/1982  Luk et al. ........................ 549/414
4,389,410  6/1983  O'Hanlon et al. ............... 549/414

Primary Examiner—Nicky Chan
Attorney, Agent, or Firm—Jacobs & Jacobs

[57] ABSTRACT

Compounds of formula (I):

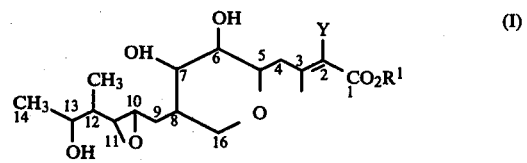

wherein
Y is halogen,
$R^1$ is hydrogen, a salt forming radical, alkyl or aralkyl,
have antibacterial and/or antimycoplasmal activity.

3 Claims, No Drawings

2-HALO-SUBSTITUTED MONIC ACID A USEFUL AS ANTIBACTERIAL COMPOUNDS

This invention relates to antibacterial compounds and in particular to a class of compounds which have antibacterial activity against certain Gram-positive and Gram-negative organisms, and also possess anti-mycoplasmal activity. The compounds are, therefore, of value in the treatment of human and veterinary infections.

The compounds of formula (A) and salts and esters thereof:

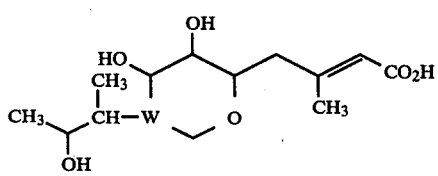

wherein W represents

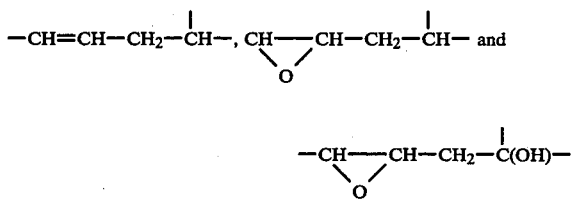

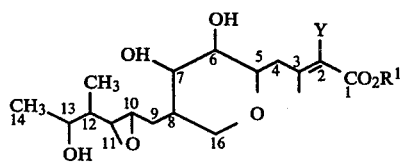

are disclosed in West Germany Offenlegungsschriften No. 2726619, 2726618 and 284868 and European Patent Application No. 793003/1.6. Compounds of formula (I) having the tri-substituted double bond in the E-configuration are referred to as monic acid C, monic acid A and monic acid B respectively.

We have now found that certain monic acid A derivatives which are substituted at the C-2 position, have antibacterial and/or antimycoplasmal activity.

According to the present invention there is provided a compound of the formula (I):

(I)

[structure of formula (I) with OH, OH, CH₃, CH₃, CH₃, OH groups and CO₂R¹ and Y substituents, numbered 2-16]

in which Y represents a halogen atom, and $R^1$ represents a hydrogen atom, a salt forming radical or alkyl or aralkyl.

Preferably Y represents fluorine, or chlorine.

Suitably $R^1$ is $C_{1-6}$ alkyl or optionally substituted phenyl ($C_{1-6}$) alkyl. Suitable substituents for phenylalkyl include halogen, $C_{1-6}$ alkyl, $C_{1-6}$ alkoxy, hydroxy, carboxy, $C_{1-6}$ alkoxycarbonyl, carbamoyl, mono- or di($C_{1-6}$) alkyl carbamoyl, sulphamoyl, mono- and di($C_{1-6}$) sulphamoyl, cyano, nitro, amino, mono- and di-($C_{1-6}$)alkylamino, $C_{1-6}$ acylamino, ureido, $C_{1-6}$ alkoxycarbonylamino, 2,2,2-trichloroethoxycarbonylamino, $C_{1-6}$ alkanoyl, $C_{1-6}$ akylthio, $C_{1-6}$ alkanesulphinyl, and $C_{1-6}$ alkanesulphonyl.

When the group $R^1$ is a salt-forming radical, the salts may be pharmaceutically acceptable, but need not be, as the utility of compounds (I) in this case is as intermediates. Suitable salts of the compounds include metal salts, e.g. aluminum, alkali metal salts, such as lithium, sodium or potassium, alkaline earth metal salts, such as calcium or magnesium, and ammonium or substituted ammonium salts for example those with lower alkyl amino such as triethylamine, hydroxy-lower alkylamines such as 2-hydroxyethylamine, bis(2-hydroxy)-amine, or tri-(2-hydroxyethyl)amine, cycloalkylamines such as bicyclohexyl-amine, or with procaine, dibenzylamine, N,N-dibenzylethylene-diamine, 1-ephenamine, N-ethyl-piperidine, N-benzyl-β-phenethyl amine, dehydroabietylamine, N,N'-bis-dehydroabietylethylenediamine, or bases of the pyridine type such as pyridine, collidine, or quinoline.

Preferred examples of the group $R^1$ are methyl, ethyl and benzyl, the latter being optionally substituted by one or more cyano, methylsulphonyl, sulphamoyl or nitro groups.

The compounds of this invention may exist in both the Z (natural) and E (or iso) geometrical forms. It is to be understood that both geometrical isomers of the compound of formula (I) are included within the scope of this invention, as well as mixtures of the two isomers. However, because in general the Z-isomer of a particular derivative of compound (I) where $R^1$ is alkyl or aralkyl has the greater activity, it is preferable to employ that isomer.

The compound of formula (I) wherein $R^1$ is hydrogen is useful as an intermediate for production of the esters.

The compounds of the present invention wherein $R^1$ is alkyl or aralkyl may be prepared by reacting a compound of formula (II) in which the hydroxyl groups may be protected,

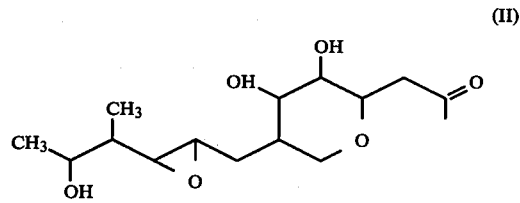

with a compound of formula (III), (IV) or (V):

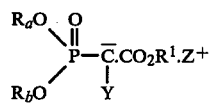

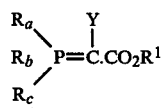

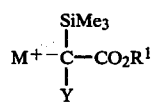

in which $Z^+$ is a counter ion, such as an alkali metal ion, $R_a$, $R_b$ and $R_c$ are the same or different and each is lower alkyl, aryl or aralkyl, $M^+$ is a metal cation, Y is as defined in formula (I) and $R^1$ is alkyl or aralkyl as defined with respect to formula (I) above; and subsequently removing any hydroxyl protecting groups.

One preferred embodiment of this process comprises reacting compound (II) with compound (III). Preferably in this case $R_a$ and $R_b$ are methyl or ethyl. In the case when compound (II) is reacted with compound (IV), then $R_a$, $R_b$ and $R_c$ are preferably all phenyl.

The reaction of a compound of formula (II) with a compound of formula (III) or (IV) is usually carried out in an inert solvent such as dimethylformamide, hexane, benzene, tetrahydrofuran, for example, at a temperature from about 0° C. to about 100° C. Under these conditions the reaction proceeds smoothly over a period from a few minutes to a few hours and the product may be isolated by any of the usual techniques, e.g. solvent evaporation or anti-solvent precipitation followed by filtration. Purification of the product may be by any of the usual chromatographic or recrystallisation techniques.

The reaction of a compound of formula (II) with a compound of formula (V) may conveniently be effected in an organic solvent, such as tetrahydrofuran or diethyl ether, at reduced or low temperature, such as from −80° to 0° C.

Preferably M+ is an alkali metal cation, most preferably a lithium or sodium cation.

Although the reaction with the compound (III), (IV) or (V) is possible with hydroxyl protection, in general higher yields of the compounds (I) are formed if the hydroxyl groups are protected. Such protecting groups must be removable under suitably mild conditions and suitable groups include silyl groups produced from a silylating agent. Suitable silylating agents are halosilanes or silazanes of the formulae:

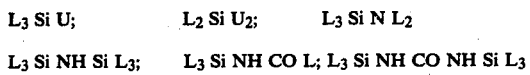

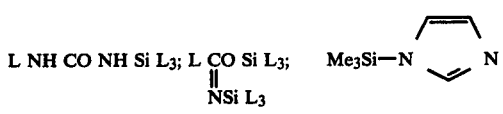

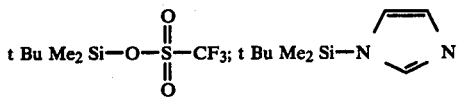

wherein U is halogen and the various groups L which may be the same or different, each represents hydrogen, or alkyl, alkoxy, aryl or aralkyl. A preferred silylating agent is trimethylsilyl chloride. Particularly suitable hydroxyl-protecting groups include trimethylsilyl, t-butyldimethylsilyl and t-butyl diphenylsilyl. A preferred hydroxyl-protecting group is trimethylsilyl, as it is readily removed on completion of the reaction.

The compounds of formula (I) where $R^1$ is hydrogen or a salt forming radical may be prepared by chemical or enzymatic hydrolysis of a compound of formula (I) wherein $R^1$ is alkyl or aralkyl, under conditions which do not disrupt the rest of the molecule.

A particularly advantageous method of carrying this hydrolysis process out for the preparation of compound (I), where $R^1$ is hydrogen or a salt forming radical comprises:
(a) protecting a compound of formula (I) wherein $R^1$ is alkyl or aralkyl, with a hydroxyl protecting group which is stable to alkaline conditions and is removable under mild acid conditions;
(b) hydrolysing the alkyl or aralkyl ester moiety $-CO_2R^1$ of the resulting compound under alkaline conditions;
(c) removing the hydroxyl protecting group; and
(d) optionally thereafter converting the acid thus formed to a salt.

The use of hydroxyl protecting group is important in the present process because the molecule of formula (I) is susceptable to rearrangement under the alkaline conditions necessary to carry out the ester hydrolysis step.

The choice of a suitable hydroxyl protecting group is also important and must (a) react with the hydroxy group; (b) be stable under alkaline conditions, and (c) be either removable under mild acidic conditions which again do not cause rearrangement of the molecule, or converted under mild acid conditions to a different group which is removable under alkaline or enzymic conditions.

Preferably the glycol moiety is protected and suitable reagents for forming the hydroxyl protecting group include compounds of formula (VI):

wherein $R^3$ is hydrogen or a $C_{1-6}$ alkyl group and $R^4$, $R^5$ and $R^6$ independently represent a $C_{1-6}$ alkyl group.

The use of the compound of formula (VI) in the hydrolysis process is illustrated in Scheme A below, where X represents the residue:

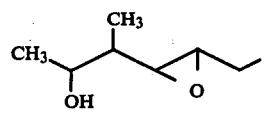

(wherein the hydroxyl group may also be protected during the reaction).

The group $R^3$ may be for example hydrogen, methyl, ethyl, n- or iso-propyl. Most suitably, $R^3$ represents hydrogen so that the compound of formula (VI) is a trialkyl orthoformate. In such a case, the groups remaining attached to the hydroxyl group in formulae (IXA) and (IXB) are formyl groups and are readily removed under mild alkaline conditions to regenerate the free hydroxyl group, without disrupting the rest of the molecule. If the group $R^3$ is a $C_{1-6}$ alkyl group the corresponding $C_{1-6}$ alkanoyl protecting groups in compounds (IXA) and (IXB) may also be removed by either a chemical or enzymatic hydrolysis procedure.

The groups $R^4$, $R^5$ and $R^6$ may be for example methyl, ethyl, n- or iso-propyl, n- or iso-, sec- or tert-butyl. Preferably $R^4$, $R^5$ and $R^6$ are all the same and each represents a methyl group and $R^3$ represents a hydrogen atom.

The alkaline hydrolsis of step (b) above may be carried out by any conventional method. Suitable bases for this step include inorganic bases, especially alkali metal hydroxides, such as sodium hydroxide, potassium hydroxide, carbonates such as potassium carbonate and bicarbonates such as sodium bicarbonate or potassium bicarbonate. The reaction is generally carried out at ambient temperature for a period from 1 to 10 hours. A suitable temperature is from 20° to 80° C. preferably from 50° to 80° C., especially from 60° C. to 70° C.

The hydroxyl protecting group is then removed by a conventional method for the particular hydroxyl protecting group, and the compound of formula (X) is isolated.

The compound of formula (X) may be converted into its salt by conventional salt forming processes.

The hydroxyl protecting group may be such that it can be removed directly or alternatively, it may be converted by mild acid treatment into a different protecting group which is then removable under alkaline conditions. This latter approach is illustrated in Scheme A wherein the glycol protecting group is converted by acid to the group —OCOR³ which is then removed.

The compounds of formula (I) wherein R¹ is alkyl or aralkyl may also be prepared by reacting a salt of the compound of formula (X) as defined above, with a compound of formula (XII):

$$R^1-Z \qquad (XII)$$

in which $R^1$ is alkyl or aralkyl as defined in formula (I) and Z is a leaving group such as a halogen atom or an alkyl or aryl sulphonate group, preferably a chlorine or bromine atom or a mesylate group.

The reaction is suitably carried out in a polar aprotic solvent such as dimethylformamide (DMF) or dimethylacetamide (DMAc).

SCHEME A

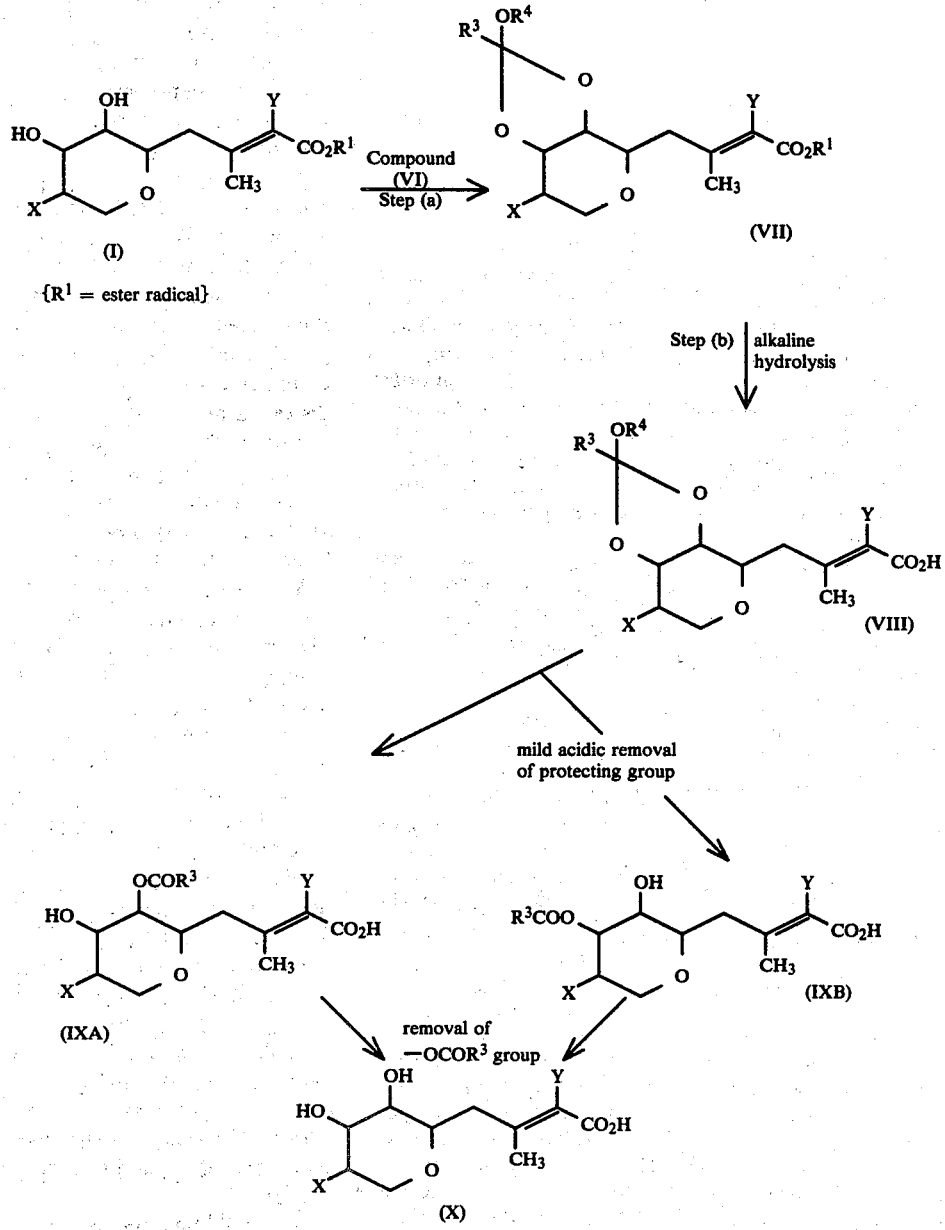

The infections against which compounds of this invention are particularly useful include venereal disease. They are also effective in the treatment of respiratory infections such as bacterial bronchitis; and bacterial meningitis, non-specific urethritis and pneumonia. In animals it may be employed for the treatment of mastitis in cattle, for swine dysentery, and for mycoplasma infections in animals such as turkeys, chickens, pigs and cattle.

Some of the human and veterinary diseases either caused by mycoplasma species or in which they play a prominent role, and against which compounds of this invention are effective, are as follows:

Avian

*M. gallisepticum*—chronic respiratory diseases (air-sacculitis) of chickens and turkeys Bovine

*M-bovis*—mastitis, respiratory disease and arthritis of cattle
*M. dispar*—calf pneumonia Porcine

*M. suipneumoniae*—enzootic pneumonia of pigs
*M. hyorhinis*—arthritis in pigs
*M. hyosynoviae*

Human

*M. pneumoniae*—primary atypical pneumonia

Compounds of the present invention are particularly useful in the treatment of enzootic pneumonia in animals such as pigs, cattle and sheep, because they also have activity against the bacteria *Bordetella bronchiseptica, Pasteurella multocida* and *Haemophilus spp*, which often cause respiratory complications in cases of this disease.

This invention also provides a pharmaceutical or veterinary composition which comprises a compound of formula (I) wherein $R^1$ is alkyl or aralkyl together with a pharmaceutically or veterinarily acceptable carrier or excipient.

The compositions may be formulated for administration by any route, and would depend on the disease being treated. The compositions may be in the form of tablets, capsules, powders, granules, lozenges, liquid or gel preparations, such as oral, topical or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin compounds of this invention may be made up into a cream, lotion or ointment. Cream or ointment formulations that may be used for compounds of formula (I) wherein $R^1$ is alkyl or aralkyl are conventional formulations well known in the art, for example, as described in standard text books of pharmaceutics and cosmetics, such as Harry's Cosmeticology published by Leonard Hill Books, and the British Pharmacopoeia.

Suppositories will contain conventional suppository bases, e.g. cocoa-butters or other glyceride.

For parenteral administration, fluid unit dosage forms are prepared utilizing the compound and a sterile vehicle. The compound, depending on the vehicle and concentration used, can either be suspended or dissolved in the vehicle. In preparing solutions the compound can be dissolved in water for injection and filter sterilized before filling into a suitable vial or ampoule and sealing. Advantageously, adjuvants such as a local anaesthetic, preservative and buffering agents can be dissolved in the vehicle. To enhance the stability the composition can be frozen after filling into the vial and water removed under vacuum. The dry lyophilized powder is then sealed in the vial. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compounds.

Veterinary compositions for intramammary treatment of mammary disorders in animals, especially bovine mastitis, will generally contain a suspension of a compound of formula (I) wherein $R^1$ is alkyl or aralkyl in an oily vehicle.

The compositions may contain from 0.1% to 99% by weight, preferably from 10–60% by weight, of the active material, depending on the method of administration. Where the compositions comprise dosage units, each unit will preferably contain from 50–500 mg, of the active ingredient. The dosage as employed for adult human treatment will preferably range from 100 mg to 3 g, per day, for instance 250 mg to 2 g, per day, depending on the route and frequency of administration.

Alternatively, a compound of formula (I) wherein $R^1$ is alkyl or aralkyl may be administered as part of the total dietary intake. In this case the amount of compound employed may be less than 1% by weight of the diet and in preferably no more than 0.5% by weight. The diet for animals may consist of normal foodstuffs to which the compound may be added or it may be added to a premix.

A suitable method of administration of a compound of formula (I) wherein $R^1$ is alkyl or aralkyl to animals is to add it to the animals' drinking water. In this case a concentration of compound in the drinking water of about 5–500 µg/ml, for example 5–200 µg/ml, is suitable.

The following Examples illustrate the invention.

EXAMPLES 1 AND 2

Ethyl-4-[5S-(2S,3S-epoxy-5S-hydroxy-4S-methylhexyl)-3R,
4R-dihydroxytetrahydropyran-2S-yl]-2-fluoro-3-methylbut-2(Z)-enoate (Ethyl 2-fluoromonate A) and
Ethyl-4-[5S-(2S,3S-epoxy-5S-hydroxy-4S-methylhexyl)-3R,
4R-dihydroxytetrahydropyran-2S-yl]-2-fluoro-3-methylbut-2(E)-enoate (Ethyl 2-fluoroisomonate A)

To a solution of 3R,4R-dihydroxy-5S-(2S,3S-epoxy-5S-hydroxy-4S-methylhexyl)tetrahydropyran-2S-yl acetone (9.06 g, 30 mmol) in dry THF (250 ml) at 0° was added triethylamine (13.0 ml, 93 mmol) followed by trimethylsilyl chloride (11.8 ml, 93 mmol) and a catalytic amount of 4-(N,N-dimethylamino)pyridine. The cooling bath was removed and the solution stirred at room temperature for a further 2½ h. After this time tlc (25% Et$_2$O/hexane) indicated the reaction to be complete. The solution was filtered, concentrated in vacuo then dissolved in dry THF (100 ml) and filtered again ready for the next stage of the reaction.

To a suspension of sodium hydride (50% in oil, 1.58 g, 33 mmol) in dry THF (50 ml) at 0° was slowly added a solution of ethyl P,P-diethylphosphonofluoro acetate (7.97 g, 33 mmol) in dry THF (50 ml). When addition was completed (20 min) the ice bath was removed and stirring was continued at room temperature for 2 h. The resulting slightly cloudy, pale orange solution was cooled to 0° and the protected ketone (from above) added dropwise. During the addition the solution cleared and darkened in colour and a syrupy material was deposited on the flask. Stirring was continued at room temperature for 15 h, then ammonium chloride solution was added, followed by extraction with ethyl acetate (3×100 ml). The organic phase was washed with brine, dried (MgSO$_4$), and the solvent removed in vacuo to give 21.2 g of crude material. Hydrolysis of the trimethylsilyl ethers was achieved by treating the crude matrial in THF/water (4:1, 200 ml) with hydrochloric acid (10 M, 2 ml) for 5 min. Aqueous sodium bicarbonate was then added and the mixture re-extracted with ethyl acetate (3×100 ml). The organic layer was washed with brine, dried (MgSO$_4$) then concentrated in vacuo to give an oil which was further purified by column chromatography on silica gel. Gradient elution using 0% to 5% methanol in dichloromethane yielded two pure major fractions. Ethyl 2-fluoroisomonate (4.12 g, 35%):

$\nu_{max}$ (liquid film) 3600–3200, 2980, 1720, 1660, 1300, 1150–1050, 755 cm$^{-1}$:

$\lambda_{max}$ 227 nm, $\epsilon$10,300: $\delta_H$(CDCl$_3$), 0.94 (3H, d, J=6 Hz, CH$_3$—17), 1.21 (3H, d, J=6 Hz, CH$_3$—14), 1.35 (4H, m+t, J=7 Hz, OCH$_2$CH$_3$), 1.68 (2H, t, J=6 Hz, CH$_2$—9), 1.95 (3H, d, J$_{H-F}$=5 Hz, CH$_3$—15), 2.00 (1H, m, CH—8), 2.70 (1H, dd, J=7, 1 Hz, CH—11), 2.80 (3H, m), 3.4–4.0 (7H, m) 4.28 (2H, q, J=7 Hz, CO$_2$CH$_2$CH$_3$):

$\delta_C$(CDCl$_3$), 12.6 (C17), 14.1 (OCH$_2$CH$_3$), 17.7 (C15, d, J=9.8 Hz), 20.7 (C14), 31.8 (C9), 33.9 (C4), 39.2 (C8), 42.8 (C12), 55.8 (C10), 61.2, 61.5 (C11, OCH$_2$), 65.5 (C16), 68.4 (C6), 70.2 (C7), 71.1 (C13), 76.4 (C5), 132.2 (C3, d, J=11.8 Hz), 144.6 (C2, d, J=252 Hz), 162.2 (C1, d, J=33.5 Hz);

m/e (Cl, NH$_3$, relative intensity), 408 (MNH$_4^+$, 35%), 391 (MH$^+$, 100), 373 (90), 355 (45), 227 (40), 183 (53). Ethyl 2-fluoro-monate (2.28 g, 19.5%):

$\nu_{max}$ (liquid film), 3600–3200, 2980, 1720, 1660, 1305, 1150–1050, 755:

$\lambda_{max}$ 227.5 nm, $\epsilon$10,100, $\delta_H$(CDCl$_3$), 0.93 (3H, d, J=6 Hz, CH$_3$—17), 1.22 (3H, d, J=6 Hz, CH$_3$—14), 1.34 (4H, m+t, J=7 Hz, OCH$_2$CH$_3$), 1.71 (2H, m, CH$_2$—9), 2.00 (1H, m, CH—8), 2.15 (3H, d, J=4 Hz, CH$_3$—15), 2.55 (2H, m, CH$_2$—4), 2.73 (1H, dd, J=6, 1 Hz, CH—11), 2.82 (1H, m, CH—10), 3.4–3.95 (7H, m), 4.26 (2H, q, J=7 Hz, OCH$_2$CH$_3$):

$\delta_C$(CDCl$_3$), 12.7 (C17), 14.2 (OCH$_2$CH$_3$), 17.2 (C15), 20.8 (C14), 31.7 (C9), 34.3 (C4, d, J=7.9 Hz), 39.3 (C8), 42.8 (C12), 55.7 (C10), 61.1, 61.3 (OCH$_2$, C11), 65.5 (C16), 69.4 (C6), 70.4 (C7), 71.3 (C13), 75.3 (C5), 130.7 (C3, d, J=11.9 Hz), 145.2 (C2, d, J=246 Hz), 161.4 (Cl, d, J=35 Hz);

m/e (relative intensity), 390 (M$^+$, 1%), 227 (46), 97 (53), 71 (60), 69 (90), 57 (49), 55 (64), 45 (90), 43 (100), 41 (94). (M$^+$ 390.2075, C$_{19}$H$_{31}$FO$_7$ requires 390.2051).

EXAMPLE 3

Sodium
4-[5S-(2S,3S-epoxy-5S-hydroxy-4S-methylhexyl)-3R,4R-di-hydroxy-tetrahydropyran-2S-yl]-2-fluoro-3-methylbut-2(Z)-enoate, (sodium 2-fluoro-monate A)

Ethyl 2-fluoromonate (415 mg, 1.06 mmol) was dissolved in trimethyl orthoformate (10 ml), a catalytic amount of p-toluene sulphonic acid added and the solution stirred for 30 minutes at room temperature. The reaction mixture was then poured into water, extracted with ethyl acetate (3×50 ml), the combined organic layers washed with sodium bicarbonate solution and brine then dried over MgSO$_4$. Solvent removal in vacuo gave an oil which was dissolved in methanol (10 ml) and treated with sodium hydroxide solution (10 ml, 1 M) for 18 hours at room temperature. The pH was then adjusted to pH 2 with dilute hydrochloric acid for 10 minutes, to pH 9.5 with dilute NaOH for 30 minutes, to pH 7 and the methanol removed in vacuo, then finally to pH 3.5 at which point the mixture was extracted with ethyl acetate (4×50 ml). Drying over MgSO$_4$ and solvent removal in vacuo gave the acid (158 mg, 0.44 mmol, 41%) which was converted to the stable sodium salt by treating with sodium bicarbonate (37 mg, 0.44 mmol) in a mixture of methanol and water;

$\nu_{max}$ (film) 3700–2700, 2970, 2920, 1590, 1395, 1110, 1050, 805 cm$^{-1}$;

$\lambda_{max}$ 216.5 nm ($\epsilon$7.400): $\delta_H$ (CD$_3$OD), 0.94 (3H, d, J=7 Hz, CH$_3$—17), 1.20 (3H, d, J=7 Hz, CH$_3$—14), 1.40 (1H, m, CH—12), 1.67 (2H, m, CH$_2$—9), 1.97 (1H, m, CH—8), 2.10 (3H, d, J=3.5, CH$_3$—15), 2.37 (1H, ddd, J=14, 10, 4 Hz, CH$_2$—4), 2.56 (1H, dt, J=14, 4 Hz, CH$_2$—4), 2.70 (1H, dd, J=8, 2.5 Hz, CH—11), 2.81 (1H, dt, J=2.5, 5 Hz, CH—10), 3.41 (1H, dd, J=9, 3 Hz), 3.50 (1H, dd, J=12, 4 Hz), 3.70–3.90 (4H, m);

$\delta_C$ (CD$_3$OD) 12.4 (C17), 17.3 (C15), 20.6 (C14), 33.0 (C9), 34.5 (C4, d, J=7.9 Hz), 41.0 (C8), 43.8 (C$_{12}$), 56.9 (C10), 61.7 (C11), 66.2 (C16), 70.6 (C6), 71.1 (C7), 71.7 (C13), 77.0 (C5), 122.2 (C3, d, J=15.7 Hz), 151.0 (C2, d, J=248 Hz), 169.2 (Cl, d, J=33.4 Hz).

EXAMPLE 4

3-Nitrobenzyl 4-[5S-(2S,3S-epoxy-5S-hydroxy-4S-methylhexyl)-3R,4R-dihydroxytetrahydropyran-2S-yl]-2-fluoro-3-methylbut-2(Z)-enoate, (m-nitrobenzyl 2-fluoromonate A)

A solution of sodium 2-fluoromonate A (170 mg, 0.44 mmol) and m-nitrobenzyl chloride (86 mg, 0.50 mmol) in DMF were stirred at room temperature for 15 h. Removal of the DMF in vacuo gave an oily residue with was dissolved in ethyl acetate, washed with sodium bicarbonate and brine then dried over $MgSO_4$. Solvent removal in vacuo gave the crude product (130 mg) which was purified by column chromatography on silica gel (2 g) using methanol/dichloromethane (0 to 3%) as eluant to yield the title compound (57.3 mg, 0.12 mmol, 26%);

$\nu_{max}$ (solution) 3600–3200, 2970, 2930, 1725, 1650, 1530, 1450, 1380, 1350, 1300, 1220, 1040, 905 cm$^{-1}$;

$\lambda_{max}$ 224 nm (16,250): $\delta_H$(CDCl$_3$) 0.94 (3H, d, J=7 Hz, CH$_3$—17), 1.22 (3H, d, J=7 Hz, CH$_3$—14), 1.34 (1H, q, J=7 Hz, CH—12), 1.70 (2H, m, CH$_2$—9), 2.00 (1H, m, CH—8), 2.19 (3H, d, J=3.5 Hz, CH$_3$—15), 2.60 (2H, m, CH$_2$—4), 2.70 (1H, dd, J=8, 1 Hz, CH—11), 2.82 (1H, td, J=5, 1 Hz, CH—10), 3.53 (1H, dd, J=10, 2 Hz), 3.80–4.00 (4H, m), 5.33 (2H, s, CH$_2$—Ar), 7.58 (1H, t, J=8 Hz, CH—5'), 7.74 (1H, d, J=8 Hz, CH—6'), 8.20 (1H, d, J=8 Hz, CH—4'), 8.27 (1H, s, CH—2'):

$\delta_C$(CDCl$_3$) 12.7 (C17), 17.3 (C15), 20.8 (C14), 31.7 (C9), 34.5 (C4, d, J=7.9 Hz), 39.3 (C8), 42.9 (C12), 55.6 (C10), 61.4 (C11), 65.2 (CH$_2$), 65.5 (C16), 69.4 (C6), 70.4 (C7), 71.4 (C13), 75.2 (C5), 123.0, 123.3 (C2', C4'Ar), 129.7 (C5'Ar), 132.7 (C3, d, J=13.8 Hz), 134.1 (C6'Ar), 137.6 (Cl'Ar), 143.0 (C2, d, J=256 Hz), 148.5 (C3'Ar), 160.7 (Cl, d, J=35 Hz):

m/e (relative intensity, CI, NH$_3$), 498 (MH$^+$, 10%), 468 (45), 227 (19), 124 (22), 106 (100).

EXAMPLE 5 t-Butyl 4-[5S-(2S,3S-epoxy-5S-hydroxy-4S-methylhexyl)-3R,4R-dihydroxytetrahydropyran-2S-yl]-2-chloro-3-methylbut-2-enoate To a solution of 3R,4R-dihydroxy-5S-(2S,3S-epoxy-5S-hydroxy-4S-methylhexyl)tetrahydropyran-2S-yl acetone (604 mg, 2.0 mmol) in dry tetrahydrofuran (20 ml) was added triethylamine (0.87 ml, 6.20 mmol), trimethylsilyl chloride (0.78 ml, 6.20 mmol) and a catalytic amount of 4-(N,N-dimethylamino)pyridine. After stirring at room temperature for 2 h the triethylamine hydrochloride was filtered off and the solution concentrated under reduced pressure. The resultant oil was taken up in anhydrous ether, filtered, solvent removed under reduced pressure, then the oil taken up in dry tetrahydrofuran ready for the next stage of the reaction.

To a solution of lithium diisopropylamide (from diisopropylamine, 0.37 ml, 2.64 mmol and n-butyl lithium, 1.65 ml of a 1.6 M solution) in tetrahydrofuran (10 ml) at −78° C. was added the t-butyl trimethylsilyl α-chloroacetate (534 mg, 2.40 mmol) in tetrahydrofuran (5 ml). After 1 h at −78° C. the tris(trimethylsilyl)protected ketone, vide supra, was added and the reaction stirred for 1 h at −78° C., then a further 1 h at room temperature. The mixture was quenched with ammonium chloride then extracted with ethyl acetate and dried over magnesium sulphate. Solvent removal under reduced pressure gave an oil which was taken up in tetrahydrofuran/water (100 ml, 4:1) and treated with acid (10 drops, concentrated hydrochloric acid) for 5 minutes. After this time the mixture was quenched with sodium bicarbonate and extracted with ethyl acetate. Drying (magnesium sulphate) and solvent removal under reduced pressure gave the crude product as a mixture of E and Z isomers. Column chromatography on silica (0–5% methanol in dichloromethane) allows separation of the isomers, giving t-butyl 2-chloro-isomonate A (483 mg, 11.1 mmol, 56%)

$\nu_{max}$ (film) 3600–3200, 2970, 2930, 1710, 1450, 1370, 1280, 1255, 1160, 1050, 1000, 900, 840, 810, 735 cm$^{-1}$;

$\lambda_{max}$ (EtOH) 231 nm (5,990);

$\delta_H$ (CDCl$_3$) 0.94 (3H, d, J=7 Hz, CH$_3$—17), 1.21 (3H, d, J=7 Hz, CH$_3$—14), 1.30 (1H, q, J=7 Hz, CH—12), 1.53 (9H, s, CO$_2$CMe$_3$), 1.55–1.80 (2H, m, CH$_2$—9), 2.03 (1H, m, CH—8), 2.07 (3H, s, CH$_3$—15), 2.39 (1H, bs, OH), 2.6–2.9 (4H, m), 3.4–4.0 (6H, m), 4.60 (1H, bd OH); $_C$ (CDCl$_3$) 12.7 (C17), 20.7 (C14), 22.8 (C15), 28.0 (CO$_2$C$\underline{Me}_3$), 31.9 (C9), 38.0 (C4), 39.1 (C8), 43.0 (C12), 55.9 (C10), 61.3 (C11), 65.7 (C16), 68.2 (C6), 70.4 (C7), 71.3 (C13), 76.0 (C5), 83.7 (CO$_2\underline{Me}_3$), 121.1 (C2), 145.6 (C3), 164.6 (C1);

m/e (CI, NH$_3$, relatively intensity) 454 (MNH$_4^+$, 4%), 452 (MNH$_4^+$, 12%), 396 (27), 381 (36), 379 (100), 363 (35), 361 (97), 343 (25), 227 (75), 209 (34) and t-butyl 2-chloromonate (16 mg, 0.04 mmol, 2%)

$\nu_{max}$ (film) 3600–3200, 2970, 2930, 1710, 1450, 1370, 1280, 1060, 1000, 910 cm$^{-1}$;

$\delta_H$(CDCl$_3$), 0.90 (3H, d, J=7 Hz, CH$_3$—17), 1.25 (3H, d, J=7H$_2$, CH$_3$—14), 1.55 (9H, s, C$\underline{Me}_3$), 2.15 (3H, s, CH$_3$—15), 2.70 (4H, m, CH—10, 11+CH$_2$—4), 3.4–4.0 (6H,m);

m/e (EI, relative intensity) 378, 380 (1%, M$^+$) 227 (26), 97 (22), 71 (24), 69 (39), 57 (100), 55 (33), 45 (29), 43 (48), 41 (57)

Found: 378.1445 C$_{17}$H$_{27}{}^{35}$ClO$_7$ requires 378.1444

BIOLOGICAL DATA

(a) Anti-mycoplasmal Activity

Table 1 shows the in vitro MIC values (μg/ml) of the compounds of Examples 1 and 2 against a number of mycoplasma organisms. The values were determined in Friis broth solidified with 0.9% agarose. The inoculum was 10$^3$ to 10$^5$ CFU and the MIC's were recorded after 6 days incubation at 37° C.

TABLE 1

| ORGANISMS | EXAMPLE NO. MIC (μg/ml) | |
|---|---|---|
|  | 1 | 2 |
| M. suipneumoniae NB12 | 0.5 | 10.0 |
| M. suipneumoniae JF435 | 0.5 | 10.0 |
| M. suipneumoniae HK(2) | 0.5 | 10.0 |
| M. suipneumoniae Str.11 | 0.5 | 5.0 |
| M. suipneumoniae J2206/183b | 0.5 | 10.0 |
| M. suipneumoniae MS16 | 0.25 | 5.0 |
| M. suipneumoniae PW/C/210 | 0.25 | 5.0 |
| M. suipneumoniae LABER | 0.25 | 5.0 |
| M. suipneumoniae UCD 1 | 0.5 | 10.0 |
| M. suipneumoniae TAM 6N | 0.5 | 10.0 |
| M. suipneumoniae ATCC 25095 | 0.5 | 10.0 |
| M. suipneumoniae NCTC 10110 | 0.5 | 10.0 |
| M. hyorhinis ATCC 23234 | 0.25 | 5.0 |
| M. hyorhinis ATCC 25021 | 0.25 | 5.0 |
| M. hyosynoviae ATCC 25591 | 0.25 | 10.0 |
| M. bovis NCTC 10131 | 0.025 | 0.25 |
| M. bovigenitalium ATCC 14173 | 0.025 | 0.5 |
| M. dispar NCTC 10125 | 0.1 | 2.5 |

TABLE 1-continued

| ORGANISMS | EXAMPLE NO. MIC (μg/ml) | |
|---|---|---|
| | 1 | 2 |
| M. gallisepticum S6 | 10.0 | 10.0 |
| M. pneumoniae ATCC 15492 | 5.0 | 10.0 |

(b) Veterinary Bacteria

Table 2 shows the MIC values (μg/ml) of the compounds of Examples 1, 2 and 4 against a number of organisms important in veterinary infections. The values were determined using a two fold serial dilutions in Diagnostic Sensitivity Test Agar with an inoculum of $10^4$ organisms and incubation for 18 hours at 37° C.

TABLE 2

| ORGANISMS | EXAMPLE NO - MIC (μg/ml) | | |
|---|---|---|---|
| | 1 | 2 | 4 |
| E. coli NCTC 10418 | >80.0 | >80.0 | >80.0 |
| E. coli E1 | >80.0 | >80.0 | >80.0 |
| S. dublin S7 | >80.0 | >80.0 | >80.0 |
| S. typhimurium S18 | >80.0 | >80.0 | >80.0 |
| Bord. bronchiseptica B08 | 80.0 | >80.0 | 80.0 |
| Bord. bronchiseptica B09 | 20.0 | >80.0 | 10.0 |
| Past. multocida PA1 | 1.3 | 40.0 | 0.625 |
| Past. multocida PA2 | 0.63 | 20.0 | 0.312 |
| Past. haemolytica PA5 | 5.0 | 80.0 | 10.0 |
| Erysipelothrix rhusiopathiae NCTC 8163 | 80.0 | 80.0 | 80.0 |
| Corynebacterium pyogenes CY1 | 80.0 | 80.0 | 80.0 |
| Staph. aureus B4 | 0.63 | 40.0 | 2.5 |
| Staph. aureus 152 | 0.63 | 40.0 | 1.25 |
| Staph. aureus Oxford | 0.63 | 40.0 | 1.25 |
| Strep. suis (group D) SPS11 | 20.0 | 80.0 | 5.0 |
| Strep. uberis SPU1 | 0.63 | 20.0 | 0.156 |
| Strep. dysgalactiae SPD1 | 1.3 | 40.0 | 0.312 |
| Strep. agalactiae SPA1 | 2.5 | 80.0 | 1.25 |
| B. subtilis ATCC 6633 | | | |

(c) Human Bacteria

Table 3 shows the MIC values (μg/ml) of the compounds of Examples 1, 2 and 4 against a number of organisms important in human infections. The values were determined by serial dilutions in nutrient agar with 5% chocolated horse blood after incubations for 18 hours at 37° C.

TABLE 3

| ORGANISMS | EXAMPLE NO - MIC (μg/ml) | | |
|---|---|---|---|
| | 1 | 2 | 4 |
| E. coli NCTC 10418 | >100.0 | >100.0 | >100.0 |
| E. coli ESS | 5.0 | 50.0 | 1.0 |
| P. mirabilis 889 | >100.0 | >100.0 | >100.0 |
| K. aerogenes A | >100.0 | >100.0 | >100.0 |
| Ps. aeruginosa NCTC 10662 | >100.0 | >100.0 | >100.0 |
| Past. multocida 1633 | 1.0 | 50.0 | 2.5 |
| Haemophilus influenzae Q1 | 0.1 | 10.0 | 0.5 |
| Haemophilus influenzae Wy21 | 0.25 | 10.0 | — |
| Neisseria catarrhalis 1502 | 0.5 | 10.0 | 0.5 |
| Bacillus subtilis 6633 | 2.5 | 100.0 | 0.5 |
| Corynebacterium xerosis 9755 | >100.0 | >100.0 | >100.0 |
| Sarcina lutea 8340 | >100.0 | >100.0 | >100.0 |
| Staph. aureus Oxford | 1.0 | 25.0 | 2.5 |
| Staph. aureus Russell | 1.0 | 50.0 | 2.5 |
| Staph. aureus W2827 | 1.0 | 50.0 | 2.5 |
| Strep. faecalis I | >100.0 | >100.0 | >100.0 |
| Strep. pyrogenes R80/421-A | 1.0 | 100.0 | 0.5 |
| Strep. 2788-B | 10.0 | >100.0 | 2.5 |
| Strep. 641848-C | 5.0 | 100.0 | 0.5 |
| Strep. pneumoniae CN33 | 2.5 | 100.0 | 0.5 |

We claim:

1. A compound of formula (I):

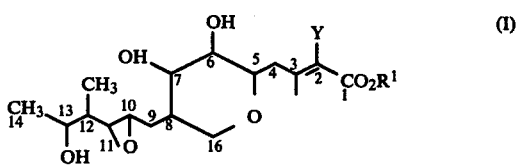

wherein
Y is halogen,
$R^1$ is hydrogen, a salt forming radical, alkyl or aralkyl.

2. A compound according to claim 1 wherein $R^1$ is ($C_{1-6}$) alkyl or optionally substituted phenyl ($C_{1-6}$) alkyl.

3. A compound according to claim 1 wherein Y is fluorine, or chlorine.

* * * * *